US012006283B2

(12) United States Patent
Suh et al.

(10) Patent No.: US 12,006,283 B2
(45) Date of Patent: Jun. 11, 2024

(54) HIF-1α INHIBITOR, PREPARATION METHOD THEREFOR, AND PHARMACEUTICAL COMPOSITION FOR PREVENTING OR TREATING ANGIOGENESIS-ASSOCIATED EYE DISEASE, CONTAINING SAME AS ACTIVE INGREDIENT

(71) Applicant: SEOUL NATIONAL UNIVERSITY R&DB FOUNDATION, Seoul (KR)

(72) Inventors: Youngger Suh, Seoul (KR); Seungbeom Lee, Seoul (KR); Jeonghun Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/057,297

(22) PCT Filed: Aug. 12, 2019

(86) PCT No.: PCT/KR2019/010208
§ 371 (c)(1),
(2) Date: Nov. 20, 2020

(87) PCT Pub. No.: WO2020/045856
PCT Pub. Date: Mar. 5, 2020

(65) Prior Publication Data
US 2021/0188753 A1 Jun. 24, 2021

(30) Foreign Application Priority Data
Aug. 31, 2018 (KR) .................. 10-2018-0103985
Aug. 8, 2019 (KR) .................. 10-2019-0096669

(51) Int. Cl.
| C07C 49/84 | (2006.01) |
| C07C 225/22 | (2006.01) |
| C07C 255/59 | (2006.01) |
| C07D 207/08 | (2006.01) |
| C07D 211/22 | (2006.01) |
| C07D 265/30 | (2006.01) |

(52) U.S. Cl.
CPC ............ *C07C 49/84* (2013.01); *C07C 225/22* (2013.01); *C07C 255/59* (2013.01); *C07D 207/08* (2013.01); *C07D 211/22* (2013.01); *C07D 265/30* (2013.01)

(58) Field of Classification Search
CPC ..... C07C 49/84; C07C 255/59; C07C 225/22; C07D 265/30; C07D 207/08; C07D 211/22
See application file for complete search history.

(56) References Cited

U.S. PATENT DOCUMENTS

2014/0309422 A1  10/2014  Ma et al.
2018/0132516 A1*  5/2018  Ray .................. A23L 29/35
2021/0188753 A1   6/2021  Suh et al.

FOREIGN PATENT DOCUMENTS

| EP | 2871187 | | 5/2015 |
| EP | 3845516 | A1 | 7/2021 |
| KR | 1020170033104 | A | 3/2017 |
| SU | 334681 | A3 | 3/1972 |
| WO | 03035635 | A1 | 5/2003 |
| WO | 2008/058269 | A2 | 5/2008 |
| WO | 2020/045856 | A1 | 3/2020 |

OTHER PUBLICATIONS

Federal Register, 79 (241), Dec. 16, 2014, pp. 74618-74633. (Year: 2014).*
Oct. 2019 Patent Eligibility Guidance Update, Oct. 2019, pp. 1-22. (Year: 2019).*
An, Hongchan, et al., "Novel Hypoxia-Inducible Factor 1α (HIF-1α) Inhibitors for Angiogenesis-Related Ocular Diseases: Discovery of a Novel Scaffold via Ring-Truncation Strategy", J. Med. Chem. (2018), 61: pp. 9266-9286. (Year: 2018).*
EESR (Extended European Search Report) dated May 10, 2022 for corresponding EP19856396.7.
Vadlapatla, et al.: "Hypoxia-Inducible Factor-1 (HIF-1): A Potential Target for Intervention in Ocular Neovascular Diseases"; Current Drug Targets, vol. 14, No. 8, May 1, 2013 (May 1, 2013), pp. 919-935, XP055696470, DOI: 10.2174/13894501113149990015. Source:.
Kim, et al.: "Ring-truncated deguelin derivatives as potent Hypoxia Inducible Factor-1a (HIF-1 a ) inhibitors"; European Journal of Medicinal Chemistry, vol. 104, Nov. 1, 2015 (Nov. 1, 2015), pp. 157-164, XP055914084, Amsterdam, NL ISSN: 0223-5234, DOI: 10.1016/j.ejmech.2015.09.033 Retrieved from the Internet: URL:https://www.sciencedirect.com/science/ article/pii/S0223523415302774?via%3Dihub>.
Jo, et al.: "Hypoxia-mediated retinal neovascularization and vascular leakage in diabetic retina is suppressed by HIF-1 a destabilization by SH-1242 and SH-1280, novel hsp90 inhibitors"; J Mol Med (Berl). Oct. 2014;92(10):1083-92. doi: 10.1007/s00109-014-1168-8. Epub May 31, 2014. PMID: 24875598.
Hong, et al.: A Versatile Synthesis of O-Desmethylangolensin Analogues from Methoxy-Substituted Benzoic Acids; Journal of the Korean Chemical Society., vol. 58, No. 6, Dec. 20, 2014 (Dec. 20, 2014), pp. 569-574, XP055697222, KR ISSN: 1017-2548, DOI: 10.5012/jkcs.2014.58.6.569 * see scheme 2 and tables; p. 572-p. 574; tables 1-2 *.
Office Action for corresponding CA3101977.

(Continued)

*Primary Examiner* — Joseph R Kosack
*Assistant Examiner* — Sagar Patel
(74) *Attorney, Agent, or Firm* — TAROLLI, SUNDHEIM, COVELL & TUMMINO L.L.P.

(57) ABSTRACT

Disclosed are a novel hypoxia-inducible factor 1α (HIF-1α) inhibitor, a method of preparing the same, and a pharmaceutical composition for preventing or treating an angiogenesis-related eye disease containing the same as an active ingredient. The compound of Example provided according to an embodiment of the present invention is capable of effectively inhibiting HIF-1α and is thus useful as a pharmaceutical composition for preventing or treating an angiogenesis-related eye disease.

5 Claims, 2 Drawing Sheets

(56) References Cited

OTHER PUBLICATIONS

Australia Patent Application No. 2019332477, Australian Office Action dated Jul. 7, 2021.
Russian Patent Application No. 2020137660, Russian Search Report, dated Feb. 25, 2021.
Russian Patent Application No. 2020137660, Russian Office Action, dated Feb. 26, 2021.
Salakka, A. et al. Synthesis of a-methyldeoxybenzoins. Journal of the Chemical Society, Accepted Jul. 30, 1999, 2601-2604.
Murphy, Stephen K. et al.; "Substrate-Directed Hydroacylation: Rhodium-Catalyzed Coupling of Vinylphenols and Nonchelating Aldehydes"; Angewandte Chemie International Edition, 2014, 53(9), 2455-2459, DOI: 10.1002/anie.201309987.
Wolters, Alexander Thomas et al.; "One-Pot, Modular Approach to Functionalized Ketones via Nucleophilic Addition of Alkyllithium Reagents to Benzamides and Pd-Catalyzed a-Arylation"; ACS Catal. 2016, 6, 4, 2622-2625, DOI: 10.1021/acscatal.6b00134.
An, Hongchan; Lee et al.; "Novel Hypoxia-Inducible Factor 1a (HIF-1a) Inhibitors for Angiogenesis-Related Ocular Diseases: Discovery of a Novel Scaffold via Ring-Truncation Strategy"; Journal of Medicinal Chemistry, 2018, 9266-9286; DOI: 10.1021/acs.jmedchem.8b00971.
VG Belikov "Pharmaceutical Chemistry", textbook, 2007, Moscow, "MEDpress-inform", p. 27-29.
M.D. Mashkovsky "Medicines", Moscow, "Medicine", 1993, part I, p. 8, left column, lines 1-6 below, right column, lines 1-13 at the top.
I.G. Smirnova et al. "Optical isomerism and biological activity of medicines", Bulletin of Moscow University, Series 2 Chemistry, 2012, 53 (3), 147-156, p. 147, left column, second paragraph.
D1_CAS Registry No. 1083197-59-4; STN Entry Date Dec. 12, 2008; 1-Propanone, 1-(2,4-dihydroxyphenyl)-2-(3-hydroxy-4-methoxyphenyl).
D2_CAS Registry No. 786622-86-4; STN Entry Date Nov. 23, 2004; Benzonitrile, 4-[2-(4-hydroxyphenyl)-1-oxopropyl].
D3_CAS Registry No. 778556-74-4; STN Entry Date Nov. 11, 2004; 1-Propanone, 2-(4-chlorophenyl)-1-(4-fluorophenyl).
D4_CAS Registry No. 770690-52-3; STN Entry Date Oct. 27, 2004; 1-Propanone, 1-(4-hydroxyphenyl)-2-(4-methylphenyl).
D5_CAS Registry No. 759439-15-1; STN Entry Date Oct. 10, 2004; 1-Propanone, 1-(4-chlorophenyl)-2-(4-hydroxyphenyl).
D6_CAS Registry No. 754167-09-4; STN Entry Date Sep. 29, 2004; 1-Propanone, 2-(4-hydroxyphenyl)-1-(4-methylphenyl).
D8_CAS Registry No. 20487-08-5; STN Entry Date Nov. 16, 1984; Propiophenone, 3',4'-dihydroxy-2-(phydroxyphenyl).
D7_CAS Registry No. 261178-38-5; STN Entry Date Apr. 6, 2000; 1-Propanone, 1-(2,4-dimethoxyphenyl)-2-[4-(2-methylpropyl)phenyl].
D9_Kang, B.C et al., 'Catalytic Asymmetric Formal Insertion of Aryldiazoalkanes into the C—H Bond of Aldehydes: Synthesis of Enantioenriched Acyclic a Tertiary Aryl Ketones', Org. Lett. (2015) 17(19), pp. 4810-4813.
D11_Cherney, A.H. et al., 'Pd-catalyzed Fukuyama cross-coupling of secondary organozinc reagents for the direct synthesis of unsymmetrical ketones', Tetrahedron 70 (2014), pp. 3259-3265.
D12_Vicario, J. L. et al., "A New General Method for the Asymmetric Synthesis of 4-Alkyl-3-aryl-1,2,3,4-tetrahydroisoquinolines", J. Org. Chem., (1999), vol. 64, doi:10.1021/jo982008I, pp. 4610-4616.
An, et al. Novel Hypoxia-Inducible Factor 1a (HIF-1a) Inhibitors for Angiogenesis-Related Ocular Diseases: Discovery of a Novel Scaffold via Ring-Truncation Strategy, J. Med. Chem. 2018, 61, 9266-9286.
Fotsis, et al. "Genisten, a dietary-derived inhibitor of in vitro angiogenesis", Proc. Natl. Acad. Sci. USA, vol. 90, pp. 2690-2694, Apr. 1993, Medical Sciences.
Hong, et al. "A Versatile Synthesis of O-Desmethylangolensin Analogues from Methoxy-Substituted Benzoic Acids", Journal of the Korean Chemical Society 2014, vol. 58, No. 6.
Vicario, et al. "A New General Method for the Asymmetric Synthesis of 4-Alkyl-3-aryl-1,2,3,4-tetrahydroisoquinolines", J. Org. Chem. 1999, 64, 4610-4616.

* cited by examiner

HIF-1α INHIBITOR, PREPARATION METHOD THEREFOR, AND PHARMACEUTICAL COMPOSITION FOR PREVENTING OR TREATING ANGIOGENESIS-ASSOCIATED EYE DISEASE, CONTAINING SAME AS ACTIVE INGREDIENT

TECHNICAL FIELD

The present invention relates to a novel hypoxia-inducible factor 1α (HIF-1α) inhibitor, a method of preparing the same, and a pharmaceutical composition for preventing or treating an angiogenesis-related eye disease containing the same as an active ingredient.

BACKGROUND ART

The term "angiogenesis" refers to a mechanism by which new blood vessels are produced from existing blood vessels, is a phenomenon that rarely occurs under normal physiological conditions and is strictly controlled, and mainly occurs during embryonic development in the process of developing fertilized eggs, wound healing in adults, changes in reproductive organs during the female reproductive cycle and the like.

In adults, endothelial cells in capillaries divide relatively poorly, and usually divide at a rate of several months to several years. Angiogenesis occurs as a complicated process through the interaction of several types of cells with water-soluble factors and extracellular matrix components.

Excessive progress of angiogenesis, which is strictly controlled in this way, may cause various diseases. New blood vessels formed in tumors provide pathways to other organs, thereby facilitating metastasis, and are known to play a crucial role in diseases such as age-related macular degeneration, diabetic retinopathy, retinopathy of prematurity, neovascular glaucoma, psoriasis, rheumatoid arthritis, or chronic inflammation, in addition to tumors.

Vascular endothelial growth factor (VEGF) is a known factor that plays a key role in angiogenesis, and it is known that VEGF can be regulated by a transcriptional regulatory factor called "HIF-1α" (hypoxia inducible factor 1, alpha) (Patent Document 1).

Therefore, there is a need to develop HIF-1a inhibitors and methods for treating, ameliorating or preventing diseases or symptoms relating thereto.

DISCLOSURE

Technical Problem

Accordingly, it is one object of the present invention to provide a compound that is capable of effectively inhibiting HIF-1a and is thus useful as a pharmaceutical composition for preventing or treating an angiogenesis-related eye disease.

It is another object of the present invention to provide a method of preparing the compound.

It is another object of the present invention to provide a pharmaceutical composition for preventing or treating an angiogenesis-related eye disease containing the compound as an active ingredient.

It is yet object of the present invention to provide a health functional food composition for preventing or ameliorating an angiogenesis-related eye disease containing the compound as an active ingredient.

Technical Solution

In accordance with the present invention, the above and other objects can be accomplished by the provision of a compound represented by the following Formula (1), or a solvate, hydrate, optical isomer or pharmaceutically acceptable salt thereof:

[Formula 1]

wherein $A^1$ and $A^2$ are each independently —H, —OH, —NO$_2$, —CN, halogen, $C_{1-10}$ straight- or branched-chain alkyl, or $C_{1-10}$ straight- or branched-chain alkoxy;

$B^1$ is —H, —OH, —NO$_2$, —CN, halogen, $C_{1-10}$ straight- or branched-chain alkyl, or $C_{1-10}$ straight- or branched-chain alkoxy; and $R^1$ is —H, —OH, —NO$_2$, —CN, halogen, $C_{1-10}$ straight- or branched-chain alkyl, $C_{1-10}$ straight- or branched-chain alkoxy, $C_{3-10}$ cycloalkyloxy, straight- or branched-chain alkylamino, heterocycloalkyl of a 5- to 10-membered ring containing at least one heteroatom selected from the group consisting of N, O and S, or $C_{1-5}$ alkylamino of $C_{6-10}$ aryl unsubstituted or substituted with at least one —CN.

In accordance with another aspect of the present invention, provided is a method of preparing the compound.

In accordance with another aspect of the present invention, provided is a pharmaceutical composition for preventing or treating an angiogenesis-related eye disease containing the compound as an active ingredient.

In accordance with another aspect of the present invention, provided is a health functional food composition for preventing or ameliorating an angiogenesis-related eye disease containing the compound as an active ingredient.

Advantageous Effects

The compound provided in an embodiment of the present invention is capable of effectively inhibiting HIF-1α and is thus useful as a pharmaceutical composition for preventing or treating an angiogenesis-related eye disease.

MODE FOR INVENTION

The present invention provides a compound represented by the following Formula (1), or a solvate, hydrate, optical isomer, or pharmaceutically acceptable salt thereof:

[Formula 1]

wherein $A^1$ and $A^2$ are each independently —H, —OH, —NO$_2$, —CN, halogen, $C_{1-10}$ straight- or branched-chain alkyl, or $C_{1-10}$ straight- or branched-chain alkoxy;

$B^1$ is —H, —OH, —NO$_2$, —CN, halogen, $C_{1-10}$ straight- or branched-chain alkyl, or $C_{1-10}$ straight- or branched-chain alkoxy; and $R^1$ is —H, —OH, —NO$_2$, —CN, halogen, $C_{1-10}$ straight- or branched-chain alkyl, $C_{1-10}$ straight- or branched-chain alkoxy, $C_{3-10}$ cycloalkyloxy, di-$C_{1-10}$ straight- or branched-chain alkylamino, heterocycloalkyl of a 5- to 10-membered ring containing at least one heteroatom selected from the group consisting of N, O and S, or $C_{1-5}$ alkylamino of $C_{6-10}$ aryl unsubstituted or substituted with at least one —CN.

The compound represented by Formula 1 of the present invention can be used in the form of a pharmaceutically acceptable salt, and an acid addition salt formed by a pharmaceutically acceptable free acid is useful as the salt. The acid addition salt is obtained from an inorganic acid such as hydrochloric acid, nitric acid, phosphoric acid, sulfuric acid, hydrobromic acid, hydroiodic acid, nitrous acid and phosphonic acid, a non-toxic organic acid such as aliphatic mono- and di-carboxylate, phenyl-substituted alkanoate, hydroxy alkanoate and alkanedioate, an aromatic acid, aliphatic and aromatic sulfonic acid, and an organic acid such as trifluoroacetic acid, acetate, benzoic acid, citric acid, lactic acid, maleic acid, gluconic acid, methanesulfonic acid, 4-toluenesulfonic acid, tartaric acid and fumaric acid.

Examples of the pharmaceutically non-toxic salt include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, p-hydroxybutyrate, glycolate, malate, tartrate, methanesulfonate, propanesulfonate, naphthalene-1-sulfonate, naphthalene-2-sulfonate, mandelate and the like.

The acid addition salt according to the present invention can be prepared by a conventional method, for example, can be prepared by dissolving the derivative of Formula 1 in an organic solvent such as methanol, ethanol, acetone, methylene chloride or acetonitrile, adding an organic or inorganic acid thereto, and filtering the resulting precipitate, followed by drying, or prepared by evaporating a solvent and an excess of acid under reduced pressure, followed by drying and crystallization in the presence of an organic solvent.

In addition, a pharmaceutically acceptable metal salt can be prepared using a base. The alkali metal or alkaline earth metal salt is obtained, for example, by dissolving a compound in an excess amount of an alkali metal hydroxide or alkaline earth metal hydroxide solution, filtering the non-dissolved compound salt, and evaporating and drying the filtrate. At this time, it is pharmaceutically preferable to prepare a sodium, potassium or calcium salt as the metal salt. In addition, the corresponding salt is obtained by reacting an alkali metal or alkaline earth metal salt with an appropriate silver salt (e.g., silver nitrate).

Further, the present invention includes all of the compound represented by Formula 1 and a pharmaceutically acceptable salt thereof, as well as a solvate, optical isomer, hydrate and the like that can be prepared therefrom.

In addition, the present invention provides a method of preparing the compound.

Furthermore, in an embodiment, the present invention provides a pharmaceutical composition for preventing or treating an angiogenesis-related eye disease containing the compound as an active ingredient. Here, some specific examples of the angiogenesis-related eye disease include, but are not limited to, macular degeneration, retinal vein occlusion, diabetic retinopathy, ischemic retinopathy, and the like.

The compound represented by Formula 1 or a pharmaceutically acceptable salt thereof may be administered in the form of any one of various oral and parenteral formulations upon clinical administration. The formulation is prepared using an ordinarily used diluent or excipient such as a filler, extender, binder, wetting agent, disintegrant or surfactant. Solid preparations for oral administration include tablets, pills, powders, granules, capsules and the like, and these solid preparations are prepared by mixing at least one compound with at least one excipient, such as starch, calcium carbonate, sucrose, lactose, or gelatin. Further, in addition to simple excipients, lubricants such as magnesium stearate and talc are also used. Liquid preparations for oral administration include suspensions, oral solvents and liquids, emulsions, syrups and the like, and various excipients, such as wetting agents, sweeteners, fragrances and preservatives, in addition to water and liquid paraffin, which are commonly used simple diluents, may be included. Formulations for parenteral administration include sterile aqueous solutions, non-aqueous solvents, suspensions, and emulsions. As the non-aqueous solvents and suspension suspensions, propylene glycol, polyethylene glycol, vegetable oil such as olive oil, and injectable ester such as ethyl oleate may be used.

The pharmaceutical composition containing the compound represented by Formula 1 or a pharmaceutically acceptable salt thereof as an active ingredient may be administered parenterally, and the parenteral administration may be carried out by subcutaneous injection, intravenous injection, intramuscular injection, or intrathoracic injection.

At this time, in order to prepare a formulation for parenteral administration, the compound represented by Formula 1 or a pharmaceutically acceptable salt thereof is mixed with water along with a stabilizer or buffer to prepare a solution or suspension and an ampoule or vial unit dosage is obtained therefrom. The composition may be sterilized and/or may contain adjuvants such as preservatives, stabilizers, hydrating agents or emulsification accelerators, and salts and/or buffers for controlling osmotic pressure, and other therapeutically beneficial substances, and may be formulated by an ordinary method such as mixing, granulation, or coating.

Formulations for oral administration include, for example, tablets, pills, hard/soft capsules, liquids/solutions, suspensions, emulsions, syrups, granules, elixirs, and troches. These formulations contain, in addition to the active ingredient, diluents (e.g., lactose, dextrose, sucrose, mannitol, sorbitol, cellulose and/or glycine) and lubricants (such as silica, talc, stearic acid and magnesium or calcium salts thereof and/or polyethylene glycol). Tablets may contain a binder such as magnesium aluminum silicate, starch paste, gelatin, methylcellulose, sodium carboxymethylcellulose, and/or polyvinylpyrrolidine, and in some cases may contain disintegrants or boiling mixtures such as starch, agar, alginic acid or sodium alginate, and/or absorbents, colorants, flavoring agents, and sweeteners.

In addition, in an embodiment, the present invention provides a health functional food composition for preventing or ameliorating an angiogenesis-related eye disease containing the compound as an active ingredient.

The compound represented by Formula 1 according to the present invention may be added to food or may be used in combination with another food or food ingredient, and may be appropriately used according to a conventional method. The amount of the active ingredient that is mixed may be appropriately determined according to the purpose of use (for prevention or amelioration) thereof. In general, the compound in the health food may be added in an amount of 0.1 to 90 parts by weight with respect to the total weight of the food. However, in the case of long-term intake for the purpose of health and hygiene or for the purpose of health regulation, the amount may be below the range defined above, and there is no problem in terms of safety, so the active ingredient may be used in an amount above the range defined above.

In addition, the health functional beverage composition of the present invention is not particularly limited to other ingredients, except that the health functional beverage composition contains the compound as an essential ingredient at a predetermined ratio, and may contain any one of various flavoring agents or natural carbohydrates, as an additional ingredient, like ordinary beverages. Examples of the natural carbohydrates include: monosaccharides such as glucose and fructose; disaccharides such as maltose and sucrose; and polysaccharides, for example, common sugars such as dextrin and cyclodextrin, and sugar alcohols such as xylitol, sorbitol and erythritol. Examples of flavoring agents that can be advantageously used other than those described above include natural flavoring agents (thaumatin, *stevia* extract (for example, rebaudioside A, glycyrrhizin or the like)) and synthetic flavoring agents (saccharin, aspartame or the like). The ratio of the natural carbohydrate is generally about 1 to 20 g, and preferably about 5 to 12 g, with respect to 100 g of the composition of the present invention.

Further, in addition to the substances described above, the compound represented by Formula 1 according to the present invention includes various nutrients, vitamins, minerals (electrolytes), flavoring agents such as synthetic flavoring agents and natural flavoring agents, coloring agents and fillers (cheese, chocolate and the like), pectic acid and salts thereof, alginic acid and salts thereof, organic acids, protective colloidal thickeners, pH adjusters, stabilizers, preservatives, glycerin, alcohols, carbonation agents used in carbonated beverages, and the like. In addition, the compound represented by Formula 1 of the present invention may contain flesh for the production of natural fruit juice, fruit juice beverages and vegetable beverages.

The exemplary compounds provided in one embodiment of the present invention are capable of effectively inhibiting HIF-1α and thus are useful as a pharmaceutical composition for preventing or treating an angiogenesis-related eye disease, which will be supported by Examples and Experimental Examples described later.

Hereinafter, the present invention will be described in detail with reference to Examples and Experimental Examples.

However, Examples and Experimental Examples described below are provided only for illustration of the present invention, and the present invention is not limited thereto.

<Example 1> Preparation of 2-(3,4-dimethoxyphenyl)-1-(4-hydroxy-2-methoxyphenyl)ethan-1-one (31)

A 2N-HCl solution (10.0 mL) was added to a solution (877 mg, 2.4 mmol) of 2-(3,4-dimethoxyphenyl)-1-(2-methoxy-4-methoxymethoxy)phenyl)ethan-1-one in methanol. The reaction mixture was stirred at 60° C. for 4 hours and extracted with EtOAc. The organic layer was collected, washed with brine, dried over anhydrous MgSO$_4$, and concentrated under reduced pressure. The residue was purified through silica gel flash column chromatography (EtOAc/n-hexane=1:1) to prepare the title compound. (723 mg, 94%)

$^1$H-NMR (CDCl$_3$, 300 MHz) δ 7.71 (d, J=8.7 Hz, 1H), 6.79-6.71 (m, 3H), 6.40-6.37 (m, 2H), 5.52 (s, 1H), 4.19 (s, 2H), 3.86 (s, 3H), 3.82 (s, 6H), 3.82 (s, 3H).

<Example 2> Preparation of 1-(2,4-dimethoxyphenyl)-2-(3,4-dimethoxyphenyl)propan-1-one (32a)

Cesium carbonate (52 mg, 0.2 mmol) and iodomethane (12.0 μL, 0.2 mmol) were added at 0° C. to a solution of the compound of Example 1 in acetonitrile (1.0 mL). The reaction mixture was stirred at 0° C. for 20 minutes and then stirred at room temperature (about 20 to 23° C.) for 1 hour. The reaction mixture was treated with water to terminate the reaction and extracted with EtOAc. The organic layer was collected, washed with brine, dried over anhydrous MgSO$_4$, and concentrated under reduced pressure. The residue was purified through silica gel flash column chromatography (EtOAc/n-hexane=1:2) to prepare the title compound as a yellow oil. (25 mg, 71%)

$^1$H-NMR (CDCl$_3$, 500 MHz) δ 7.60 (d, J=8.7 Hz, 1H), 6.72 (m, 3H), 6.42 (dd, J=8.7, 2.2 Hz, 1H), 6.35 (d, J=2.2 Hz, 1H), 4.68 (q, J=7.0 Hz, 1H), 3.81 (s, 3H), 3.80 (s, 3H), 3.79 (s, 3H), 1.44 (d, J=7.0 Hz, 3H); $^{13}$C-NMR (CDCl$_3$, 125 MHz) δ 201.8, 163.9, 159.8, 148.7, 147.6, 134.6, 132.8, 121.5, 120.2, 111.2, 111.0, 104.9, 98.3, 55.8, 55.7, 55.4, 55.3, 50.6, 19.1; HR-MS (ESI) calcd for C$_{19}$H$_{23}$O$_5$ (M+H+) 331.1540, found 331.1537.

<Example 3> Preparation of 2-(3,4-dimethoxyphenyl)-1-(4-ethoxy-2-methoxyphenyl)propan-1-one (32b)

The title compound was obtained as a pale yellow oil (10 mg, 91%) through a similar process to Example 2, except that iodoethane (5.0 μL, 0.1 mmol) was used, instead of iodomethane.

$^1$H-NMR (CDCl$_3$, 800 MHz) δ 7.60 (d, J=8.7 Hz, 1H), 6.73 (m, 3H), 6.41 (dd, J=8.7, 2.2 Hz, 1H), 6.35 (d, J=2.2 Hz, 1H), 4.68 (q, J=6.9 Hz, 1H), 4.01 (q, J=7.0 Hz, 1H), 3.81 (s, 6H), 3.80 (s, 3H), 1.44 (d, J=7.0 Hz, 3H), 1.38 (t, J=7.0 Hz, 3H); $^{13}$C-NMR (CDCl$_3$, 200 MHz) δ 201.8, 163.3, 159.8, 148.7, 147.5, 134.6, 132.8, 121.2, 120.2, 111.1, 110.9, 105.4, 98.8, 63.6, 55.7, 55.7, 55.3, 50.5, 19.1, 14.6; HR-MS (ESI) calcd for C$_{20}$H$_{25}$O$_5$ (M+H+) 345.1697, found 345.1695.

<Example 4> Preparation of 1-(4-(cyclohexyloxy)-2-methoxyphenyl)-2-(3,4-dimethoxyphenyl)propan-1-one (32c)

A solution of diethyl azodicarboxylate (0.02 mL, 0.1 mmol) in THF (1.0 mL) was added to a solution of the compound of Example 1 (26 mg, 0.1 mmol), cyclohexanol (9 μL, 0.1 mmol) and triphenylphosphine (22 mg, 0.1 mmol) in THF (1.0 mL). The reaction mixture was stirred for one day and concentrated under reduced pressure. The residue was purified through silica gel flash column chromatography (EtOAc/n-hexane=1:6) to prepare the title compound as a colorless oil. (42 mg, 43%)

$^1$H-NMR (CDCl$_3$, 500 MHz) δ 7.59 (d, J=8.7 Hz, 1H), 6.73 (m, 3H), 6.41 (dd, J=8.7, 2.1 Hz, 1H), 6.34 (d, J=2.1 Hz, 1H), 4.69 (q, J=6.9 Hz, 1H), 4.26-4.22 (m, 1H), 3.80 (s, 6H), 3.79 (s, 3H), 1.96-1.90 (m, 2H), 1.79-1.73 (m, 2H), 1.54-1.46 (m, 2H), 1.33-1.27 (m, 4H); $^{13}$C-NMR (CDCl$_3$, 125 MHz) δ 201.7, 162.4, 160.0, 148.8, 147.6, 134.7, 132.8, 121.0, 120.2, 111.2, 111.0, 106.3, 100.0, 75.4, 55.8 (two carbons), 55.3, 50.5, 31.7, 31.6, 25.4, 23.6 (two carbons), 19.2; HR-MS (ESI) calcd for C$_{24}$H$_{31}$O$_5$ (M+H+) 399.2166, found 399.2164.

<Example 5> Preparation of 2-(3,4-dimethoxyphenyl)-1-(4-(dimethylamino)-2-methoxyphenyl)propan-1-one (34a)

4-(2-(3,4-dimethoxyphenyl)propanoyl)-3-methoxyphenyl trifluoromethanesulfonate (20 mg, 0.04 mmol) was treated with dimethylamine (2.0M THF solution, 0.23 mL, 0.5 mmol) to conduct amination and the resulting product was purified through silica gel flash column chromatography (EtOAc/n-hexane=1:3 to 1:1) to prepare the title compound as a yellow oil. (6 mg, 41%)

$^1$H-NMR (CDCl$_3$, 800 MHz) δ 7.71 (d, J=8.9 Hz, 1H), 6.79 (s, 1H), 6.78 (d, J=8.2 Hz, 1H), 6.72 (d, J=8.2 Hz, 1H), 6.22 (dd, J=8.9, 2.2 Hz, 1H), 5.98 (d, J=2.0 Hz, 1H), 4.74 (q, J=7.0 Hz, 1H), 3.82 (s, 3H), 3.81 (s, 3H), 3.79 (s, 3H), 2.99 (s, 6H), 1.42 (d, J=7.0 Hz, 3H); $^{12}$C-NMR (CDCl$_3$, 200 MHz) δ 200.3, 160.7, 154.4, 148.6, 147.3, 135.6, 133.2, 120.1, 115.9, 111.1, 110.9, 104.3, 93.8, 55.7 (two carbons), 54.9, 50.0, 40.0 (two carbons), 19.6; HR-MS (ESI) calcd for C$_{20}$H$_{26}$NO$_4$ (M+H+) 344.1856, found 344.1860.

<Example 6> Preparation of 2-(3,4-dimethoxyphenyl)-1-(2-methoxy-4-(pyrrolidin-1-yl)phenyl)propan-1-one (34b)

4-(2-(3,4-dimethoxyphenyl)propanoyl)-3-methoxyphenyl trifluoromethanesulfonate (20 mg, 0.04 mmol) was treated with pyrrolidine (7 μL, 0.1 mmol) to conduct amination and the resulting product was purified through silica gel flash column chromatography (EtOAc/n-hexane=1:2 to 1:1) to prepare the title compound as a pale yellow oil. (19 mg, 90%)

$^1$H NMR (CDCl$_3$, 300 MHz) δ 7.67 (dd, J=8.7, 1.2 Hz, 1H), 6.75-6.65 (m, 3H), 6.04 (dd, J=8.7, 2.0 Hz, 1H), 5.79 (s, 1H), 4.69 (q, J=6.9 Hz, 1H), 3.77-3.72 (m, 9H), 3.24-3.22 (m, 4H), 1.97-1.90 (m, 4H), 1.37 (d, 3H, J=6.9 Hz); $^{13}$C NMR (CDCl$_3$, 200 MHz) δ 200.1, 160.9, 152.0, 148.6, 147.3, 135.7, 133.4, 120.1, 115.3, 111.1, 110.9, 104.4, 93.6, 55.7 (two carbons), 54.9, 49.9, 47.5 (two carbons), 25.3 (two carbons), 19.7; HR-MS (FAB) calcd for C$_{22}$H$_{28}$NO$_4$ (M+H+) 370.2018, found 370.2032.

<Example 7> Preparation of 2-(3,4-dimethoxyphenyl)-1-(2-methoxy-4-(piperidin-1-yl)phenyl)propan-1-one (34c)

4-(2-(3,4-dimethoxyphenyl)propanoyl)-3-methoxyphenyl trifluoromethanesulfonate (20 mg, 0.04 mmol) was treated with piperidine (8 μL, 0.1 mmol) to conduct amination and the resulting product was purified through silica gel flash column chromatography (EtOAc/n-hexane=1:2) to prepare the title compound as a pale yellow oil. (10 mg, 45%)

$^1$H-NMR (CDCl$_3$, 300 MHz) δ 7.61 (d, J=8.7 Hz, 1H), 6.73-6.65 (m, 3H), 6.35 (dd, J=8.7, 2.1 Hz, 1H), 6.16 (d, J=1.8 Hz, 1H), 4.67 (q, J=6.9 Hz, 1H), 3.76 (s, 6H), 3.75 (s, 3H), 3.21-3.20 (m, 4H), 1.65-1.60 (m, 6H), 1.37 (d, 3H, J=6.9 Hz); $^{13}$C NMR (CDCl$_3$, 200 MHz) δ 200.5, 160.4, 155.5, 148.6, 147.3, 135.3, 133.0, 120.1, 117.4, 111.1, 110.9, 106.8, 96.8, 55.7 (two carbons), 55.0, 50.1, 48.8 (two carbons), 25.4 (two carbons), 24.3, 19.5; HR-MS (FAB) calcd for C$_{23}$H$_{30}$NO$_4$ (M+H+) 384.2175, found 384.2170.

<Example 8> Preparation of 2-(3,4-dimethoxyphenyl)-1-(2-methoxy-4-morpholinophenyl)propan-1-one (34d)

4-(2-(3,4-dimethoxyphenyl)propanoyl)-3-methoxyphenyl trifluoromethanesulfonate (20 mg, 0.04 mmol) was treated with morpholine (4 mg, 0.04 mmol) to conduct amination and the resulting product was purified through silica gel flash column chromatography (EtOAc/n-hexane=1:2 to 2:1) to prepare the title compound as a yellow oil. (7 mg, 53%)

$^1$H-NMR (CDCl$_3$, 800 MHz) δ 7.65 (d, J=8.8 Hz, 1H), 6.75 (m, 2H), 6.72 (d, J=8.0 Hz, 1H), 6.40 (dd, J=8.9, 2.2 Hz, 1H), 6.23 (d, J=2.2 Hz, 1H), 4.70 (q, J=6.9 Hz, 1H), 3.82 (s, 3H), 3.90-3.70 (m, 10H), 3.22 (dd, J=5.9, 3.9 Hz, 4H), 1.43 (d, J=7.0 Hz, 3H); $^{13}$C-NMR (CDCl$_3$, 200 MHz) δ 200.9, 160.1, 155.2, 148.7, 147.4, 135.0, 132.9, 120.2, 119.0, 111.1, 110.9, 106.6, 96.9, 66.5 (two carbons), 55.7, 55.7, 55.1, 50.3, 47.7 (two carbons), 19.4; HR-MS (ESI) calcd for C$_{22}$H$_{28}$NO$_5$ (M+H+) 386.1962, found 386.1963.

<Example 9> Preparation of 1-(4-(benzylamino)-2-methoxyphenyl)-2-(3,4-dimethoxyphenyl)propan-1-one (34e)

4-(2-(3,4-dimethoxyphenyl)propanoyl)-3-methoxyphenyl trifluoromethanesulfonate (20 mg, 0.04 mmol) was treated with benzylamine (0.01 mL, 0.084 mmol) to conduct amination and the resulting product was purified through silica gel flash column chromatography (EtOAc/n-hexane=1:2) to prepare the title compound as a yellow oil. (20 mg, 88%)

$^1$H-NMR (Acetone-d6, 300 MHz) δ 7.55 (d, 1H, J=8.6 Hz), 7.39-7.36 (m, 2H), 7.33-7.28 (m, 2H), 7.22 (m, 1H), 6.86 (d, 1H, J=1.8 Hz), 6.78-6.70 (m, 2H), 6.26-6.18 (m, 3H), 4.78 (q, 1H, J=6.9 Hz), 4.40 (d, 2H, J=5.6 Hz), 3.79 (s, 3H), 3.74 (s, 3H), 3.71 (s, 3H), 1.33 (d, 3H, J=6.9 Hz); $^{13}$C-NMR (CDCl$_3$, 200 MHz) δ 200.4, 160.8, 152.9, 148.7, 147.4, 138.3, 135.4, 133.5, 128.8 (two carbons), 127.5, 127.4 (two carbons), 120.1, 117.4, 111.2, 110.9, 105.1, 94.7, 55.8 (two carbons), 55, 50, 47.7, 19.6; HRMS (FAB) calcd for C$_{25}$H$_{28}$NO$_4$ (M+H+): 406.2018, Found: 406.2024.

\<Example 10\> Preparation of 4-(((4-(2-(3,4-dimethoxyphenyl)propanoyl)phenyl)amino)methyl)benzonitrile (34f)

4-(2-(3,4-dimethoxyphenyl)propanoyl)-3-methoxyphenyl trifluoromethanesulfonate (20 mg, 0.04 mmol) was treated with 4-cyanobenzylamine (10.8 mg, 0.082 mmol) to conduct amination and the resulting product was purified through silica gel flash column chromatography (EtOAc/n-hexane=1:2) to prepare the title compound as a yellow oil. (16 mg, 91%)

$^1$H-NMR (CDCl$_3$, 800 MHz) δ 7.61 (d, 1H, J=8.6 Hz), 7.60 (d, 2H, J=8.2 Hz), 7.41 (d, 2H, J=8.2 Hz), 6.76 (s, 1H), 6.74 (d, 1H, J=1.9 Hz), 6.72 (d, 1H, J=8.0 Hz), 6.10 (dd, 1H, J=8.6, 2.2 Hz), 5.94 (d, 1H, J=2.1 Hz), 4.68 (q, 1H, J=7.0 Hz), 4.58 (t, 1H, J=5.8 Hz), 4.42 (d, 2H, J=5.8 Hz), 3.80 (s, 3H), 3.80 (s, 3H), 3.72 (s, 3H), 1.41 (d, 3H, J=7.0 Hz); $^{13}$C-NMR (CDCl$_3$, 200 MHz) δ 200.6, 160.6, 152.2, 148.7, 147.4, 144.1, 135.2, 133.6, 132.6 (two carbons), 127.6 (two carbons), 120.2, 118.6, 118.1, 111.4, 111.2, 110.9, 105.0, 95.1, 55.8 (two carbons), 55.0, 50.2, 47.2, 19.6; HRMS (ESI) calcd for C$_{26}$H$_{26}$N$_2$O$_4$ (M+H+): 430.1893, Found: 430.1887.

\<Example 11\> Preparation of 2-(3,4-dimethoxyphenyl)-1-(4-(pyrrolidin-1-yl)phenyl)propan-1-one (37a)

1-(4-bromophenyl)-2-(3,4-dimethoxyphenyl)propan-1-one (23 mg, 0.1 mmol) was treated with pyrrolidine (15 μL, 0.2 mmol) to conduct amination and the resulting product was purified through silica gel flash column chromatography (EtOAc/n-hexane=1:6) to prepare the title compound as a pale yellow oil. (11 mg, 57%)

$^1$H-NMR (CDCl$_3$, 500 MHz) δ 7.87 (d, J=8.9 Hz, 2H), 6.83 (dd, J=8.1, 1.8 Hz, 1H), 6.79 (d, J=1.8 Hz, 1H), 6.74 (d, J=8.2 Hz, 1H), 6.42 (d, J=8.9 Hz, 2H), 4.55 (q, J=6.8 Hz, 1H), 3.82 (s, 3H), 3.79 (s, 3H), 3.29 (t, J=6.6 Hz, 4H), 2.00-1.96 (m, 4H), 1.46 (d, J=6.8 Hz, 3H); $^{13}$C NMR (CDCl$_3$, 125 MHz) δ 198.4, 150.7, 149.0, 147.6, 135.3, 131.0, 131.0, 123.8, 119.8, 111.3, 110.6, 110.6, 110.5, 55.8, 55.8, 47.4, 47.4, 46.2, 25.3, 25.3, 19.6; HR-MS (FAB) calcd for C$_{21}$H$_{26}$NO$_3$ (M+H+) 340.1913, found 340.1904.

\<Example 12\> Preparation of 2-(3,4-dimethoxyphenyl)-1-(4-morpholinophenyl)propan-1-one (37b)

1-(4-bromophenyl)-2-(3,4-dimethoxyphenyl)propan-1-one (23 mg, 0.1 mmol) was treated with morpholine (5 mg, 0.1 mmol) to conduct amination and the resulting product was purified through silica gel flash column chromatography (EtOAc/n-hexane=1:2 to 1:1) to prepare the title compound as a yellow oil. (12 mg, 80%)

$^1$H-NMR (CDCl$_3$, 800 MHz) δ 7.88 (d, J=9.1 Hz, 2H), 6.81 (dd, J=8.2, 2.1 Hz, 1H), 6.76 (m, 4H), 4.54 (q, J=6.8 Hz, 1H), 3.82 (s, 3H), 3.79 (s, 6H), 3.23 (t, J=5.0 Hz, 4H), 1.45 (d, J=6.9 Hz, 3H); $^{13}$C-NMR (CDCl$_3$, 200 MHz) δ 198.7, 153.9, 149.1, 147.7, 134.7, 130.7 (two carbons), 127.1, 119.9, 113.2 (two carbons), 111.3, 110.5, 66.5 (two carbons), 55.8, 55.8, 47.4 (two carbons), 46.7, 19.5; HR-MS (ESI) calcd for C$_{21}$H$_{26}$NO$_4$ (M+H+) 356.1856, found 356.1851.

\<Example 13\> Preparation of 2-(2-fluorophenyl)-1-(4-(piperidin-1-yl)phenyl)propan-1-one (41a)

1-(4-bromophenyl)-2-(2-fluorophenyl)propan-1-one (31 mg, 0.1 mmol) was treated with piperidine (15 μL, 0.2 mmol) to conduct amination and the resulting product was purified through silica gel flash column chromatography (EtOAc/n-hexane=1:5) to prepare the title compound as a yellow solid. (24 mg, 68%)

$^1$H-NMR (CDCl$_3$, 800 MHz) δ 7.85 (d, 2H, J=9.0 Hz), 7.24-7.22 (m, 1H), 7.15-7.12 (m, 1H), 7.02 (d, 1H, J=8.3 Hz), 7.01 (d, 1H, J=8.2 Hz), 6.76 (d, 2H, J=9.0 Hz), 4.96 (q, 1H, J=6.9 Hz), 3.30 (s, 4H), 1.61 (s, 6H), 1.47 (d, 3H, J=6.9 Hz); $^{13}$C-NMR (CDCl$_3$, 200 MHz) δ 197.8, 159.6 (d, JC-F=243 Hz), 154.2, 130.7, 129.3, 129.2, 128.9 (d,

JC-F=3.9 Hz), 128.2, 128.1, 125.2, 124.5 (d, JC-F=3.3 Hz), 115.4 (d, JC-F=22.5 Hz), 113.2, 48.4, 38.4, 38.4, 25.3 (two carbons), 24.3, 18.2;

<Example 14> Preparation of 1-(4-(benzylamino) phenyl)-2-(2-fluorophenyl)propan-1-one (41b)

1-(4-bromophenyl)-2-(2-fluorophenyl)propan-1-one (24 mg, 0.1 mmol) was treated with morpholine (13 μL, 0.1 mmol) to conduct amination and the resulting product was purified through silica gel flash column chromatography (EtOAc/n-hexane=1:5) to prepare the title compound as a white solid. (18 mg, 71%)

$^1$H-NMR (CDCl$_3$, 600 MHz) δ 7.83-7.82 (m, 2H), 7.33-7.25 (m, 5H), 7.22-7.21 (m, 2H), 7.15-7.12 (m, 2H), 7.02-6.99 (m, 2H), 6.52-6.51 (m, 2H), 4.94 (q, 1H, J=8.6 Hz), 4.53 (broad, 1H), 4.33 (s, 2H), 1.46 (d, 3H, J=6.9 Hz); $^{13}$C-NMR (CDCl$_3$, 150 MHz) δ 197.7, 159.6 (d, JC-F=243 Hz), 151.8, 138.1, 131.0, 131.0, 129.2 (d, JC-F=15.0 Hz), 128.8 (d, JC-F=4.3 Hz), 128.7, 128.7, 128.1 (d, JC-F=7.8 Hz), 127.5, 127.3, 127.3, 125.6, 124.5, (d, JC-F=3.5 Hz), 115.3 (d, JC-F=22.2 Hz), 111.6, 111.6, 47.5, 38.3 (d, JC-F=2.1 Hz), 18.2; HRMS (ESI) calcd for C$_{22}$H$_{21}$FNO (M+H+): 334.1607, Found: 334.1611.

<Example 15> Preparation of 2-(2-fluorophenyl)-1-(2-methoxy-4-(piperidin-1-yl)phenyl)propan-1-one LR-MS (ESI) calcd for C$_{21}$H$_{25}$FNO$_2$ (M+H+) 342.4, found 342.4.

<Example 16> Preparation of 4-(((4-(2-(2-fluorophenyl)propanoyl)-3-methoxyphenyl) amino)methyl)benzonitrile

LR-MS (ESI) calcd for C$_{24}$H$_{22}$FN$_2$O$_2$ (M+H+) 389.4, found 389.4.

The structures of the compounds of Examples 1 to 16 compound described above are shown in Table 1 below:

TABLE 1

| Example | Structure |
|---|---|
| 1 | ![structure] |
| 2 | ![structure] |
| 3 | ![structure] |
| 4 | ![structure] |

TABLE 1-continued

| Example | Structure |
|---|---|
| 5 |  |
| 6 |  |
| 7 |  |
| 8 |  |
| 9 |  |
| 10 |  |
| 11 |  |
| 12 |  |
| 13 |  |
| 14 |  |
| 15 |  |

TABLE 1-continued

| Example | Structure |
|---------|-----------|
| 16 |  |

<Comparative Example 1> Preparation of SH-1242 (2) Compound

The compound of Comparative Example 1 was prepared with reference to the literature ((J. Mol. Med. (Berl.) 2014, 92, 1083-1092 (Hypoxia-mediated retinal neovascularization and vascular leakage in diabetic retina is suppressed by HIF-1α destabilization by SH-1242 and SH-1280, novel hsp90 inhibitors)).

<Experimental Example 1> Evaluation of HIF-La Inhibitory Activity (In Vitro)

The following experiment was performed in order to evaluate inhibitory activity against HIF-1α (hypoxia-inducible factor 1α) of the compound of Example according to an embodiment of the present invention.

The results are shown in Table 2 below.

TABLE 2

| Example | $IC_{50}$ (µM) |
|---------|----------------|
| 1 | >15 |
| 2 | >15 |
| 3 | 11.68 |
| 4 | 2.59 |
| 5 | >15 |
| 6 | 2.82 |
| 7 | 1.85 |
| 8 | 8.74 |
| 9 | 1.43 |
| 10 | 0.60 |
| 11 | 2.61 |
| 12 | 6.85 |
| 13 | 2.06 |
| 14 | 7.35 |
| 15 | 6.52 |
| 16 | 5.28 |

As can be seen from Table 2 above, the compound of Example according to an embodiment of the present invention exhibits excellent inhibitory activity against HIF-1α (hypoxia-inducible factor 1α). In particular, among the compounds of Example, the compound of Example 10 exhibits the best inhibitory activity against HIF-1a.

<Experimental Example 2> Evaluation of Inhibitory Activity Against Angiogenesis (In Vitro)

The following experiment was performed in order to evaluate inhibitory activity against angiogenesis of the compound of Example according to an embodiment of the present invention.

Figure 1:
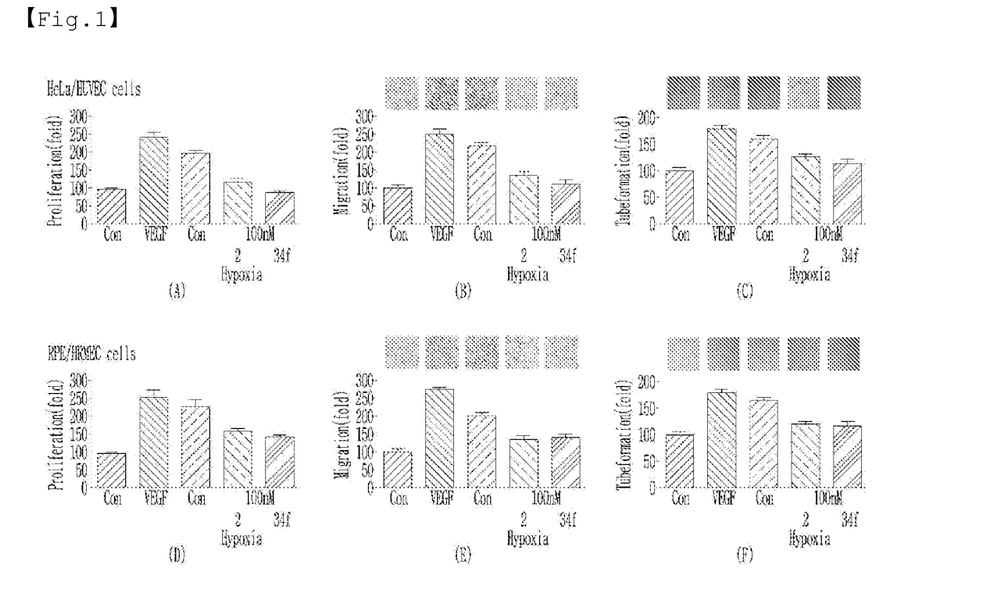
FIG. 1 is a graph showing the results of analysis of the inhibitory activity against angiogenesis of a compound of Example according to an embodiment of the present invention.

The results are shown in FIG. 1.

FIG. 1 is a graph showing the results of analysis of inhibitory activity against angiogenesis of the compound of Example according to an embodiment of the present invention, wherein compound 2 is a compound of Comparative Example 1, and compound 34f is a compound of Example 10.

As can be seen from FIG. 1, the compound of Example 10 compound according to the present invention has better inhibitory activity against angiogenesis than that of the compound of Comparative Example 1.

<Experimental Example 3> Evaluation of HIF-1α Regulatory Activity (In Vitro)

The following experiment was performed in order to evaluate regulatory activity of HIF-1α (hypoxia-inducible factor 1α) of the compound of Example according to an embodiment of the present invention.

Figure 2:
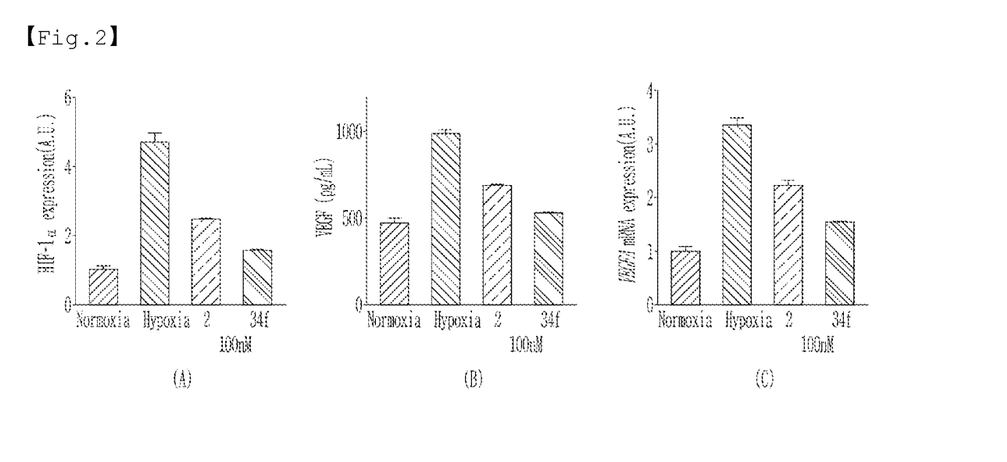
FIG. 2 is a graph showing the results of analysis of HIF-1α (hypoxia-inducible factor 1α) regulatory activity of the compound of Example according to an embodiment of the present invention.

The results are shown in FIG. 2.

FIG. 2 is a graph showing the results of analysis of the regulatory activity of HIF-1α (hypoxia-inducible factor 1α) of the compound of Example according to an embodiment of the present invention, wherein compound 2 is a compound of Comparative Example 1, and compound 34f is a compound of Example 10.

As can be seen from FIG. 2, the compound of Example 10 compound according to the present invention has better HIF-1α regulatory activity than that of the compound of Comparative Example 1.

<Experimental Example 4> Evaluation of Inhibitory Activity Against Retinal Neovascularization by Hypoxia The following experiment was performed in order to evaluate inhibitory activity against retinal neovascularization by hypoxia of the compound of Example according to an embodiment of the present invention.

Figure 3:
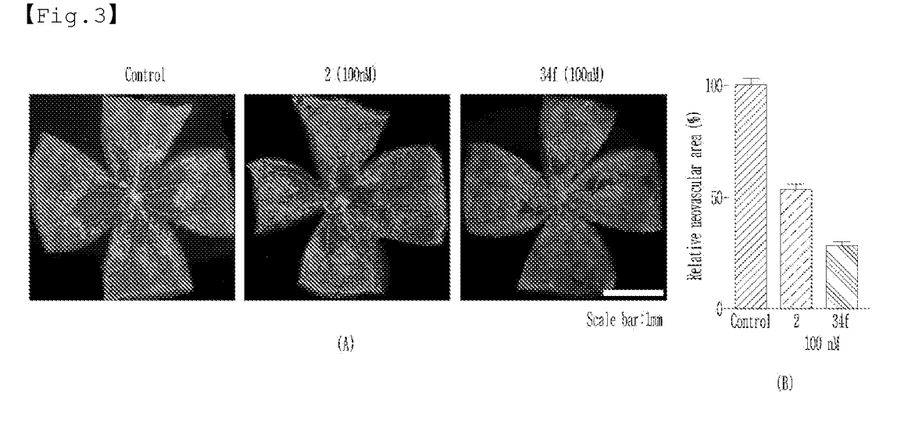
FIG. 3 is a graph showing the results of analysis of the inhibitory activity against retinal neovascularization due to hypoxia of the compound of Example according to an embodiment of the present invention.

The results are shown in FIG. 3.

FIG. 3 is a graph showing the results of analysis of the inhibitory activity against retinal neovascularization by hypoxia of the compound of Example according to an embodiment of the present invention, wherein compound 2 is a compound of Comparative Example 1, and compound 34f is a compound of Example 10.

As can be seen from FIG. 3, the compound of Example 10 compound according to the present invention has better inhibitory activity against retinal neovascularization by hypoxia than that of the compound of Comparative Example 1.

<Formulation Example 1> Preparation of Pharmaceutical Formulation 1-1. Preparation of Powder

| | |
|---|---|
| Compound of Formula 1 | 500 mg |
| Lactose | 100 mg |
| Talc | 10 mg |

The ingredients described above are mixed and the resulting mixture is charged in an airtight fabric to prepare a powder.

1-2. Preparation of Tablet

| | |
|---|---|
| Compound of Formula 1 | 500 mg |
| Corn starch | 100 mg |
| Lactose | 100 mg |
| Magnesium stearate | 2 mg |

The ingredients described above are mixed and the resulting mixture is subjected to tableting according to a conventional tablet preparation method to prepare a tablet.

1-3. Preparation of Capsule

| | |
|---|---|
| Compound of Formula 1 | 500 mg |
| Cornstarch | 100 mg |
| Lactose | 100 mg |
| Magnesium stearate | 2 mg |

The ingredients described above are mixed by a conventional capsule preparation method and the resulting mixture is charged in a gelatin capsule to prepare a capsule.

1-4. Preparation of Injection

| | |
|---|---|
| Compound of Formula 1 | 500 mg |
| Sterile distilled water for injection | appropriate amount |
| pH adjuster | appropriate amount |

An injection is prepared by charging the amounts of ingredients described above in each ample (2 mL) according to a conventional injection preparation method.

1-5. Preparation of Liquid/Solution

| | |
|---|---|
| Compound of Formula 1 | 100 mg |
| Isomerized sugar | 10 g |
| Mannitol | 5 g |
| Purified water | appropriate amount |

According to a conventional liquid preparation method, each ingredient is dissolved in purified water, an appropriate amount of lemon flavor is added to the resulting solution, the ingredients are mixed together, purified water is added thereto to adjust the total amount to 100 mL, and the resulting mixture is charged in a brown vial, followed by sterilization to prepare a liquid.

The invention claimed is:

1. A compound represented by the following Formula (1), or a solvate, hydrate, optical isomer or pharmaceutically acceptable salt thereof:

[Formula 1]

$A^1$ and $A^2$ are methoxy or $A^1$ is H and $A^2$ is F;

$B^1$ is —H, or $C_{1-10}$ straight- or branched-chain alkoxy; and

$R^1$ is $C_{3-10}$ cycloalkyloxy, heterocycloalkyl of a 5- to 10-membered ring containing at least one heteroatom selected from the group consisting of N, O and S, or benzylamino unsubstituted or substituted with —CN.

2. The compound or a solvate, hydrate, optical isomer, or pharmaceutically acceptable salt thereof according to claim 1, wherein $B^1$ is $C_{1-10}$ straight- or branched-chain alkoxy, and $R^1$ is heterocycloalkyl of a 5-membered ring containing N.

3. The compound or a solvate, hydrate, optical isomer, or pharmaceutically acceptable salt thereof according to claim 1, wherein the compound of Formula 1 is selected from the group consisting of the following compounds:

4. A method of treating or preventing an angiogenesis-related eye disease in a subject, the method comprising administering a pharmaceutically effective amount of the compound according to claim 1 to the subject.

5. The method according to claim 4, wherein the angiogenesis-related eye disease is age-related macular degeneration, diabetic retinopathy, retinopathy of prematurity, or neovascular glaucoma.

* * * * *